(12) United States Patent
Tank et al.

(10) Patent No.: US 7,316,990 B2
(45) Date of Patent: Jan. 8, 2008

(54) HIGH-STRENGTH, LOW VISCOSITY HERBICIDAL FORMULATIONS OF GLYPHOSATE

(75) Inventors: Holger Tank, Zionsville, IN (US); Sudhakar Balijepalli, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 336 days.

(21) Appl. No.: 10/774,238

(22) Filed: Feb. 6, 2004

(65) Prior Publication Data

US 2005/0032649 A1 Feb. 10, 2005

Related U.S. Application Data

(60) Provisional application No. 60/493,554, filed on Aug. 4, 2003.

(51) Int. Cl.
*A01N 57/18* (2006.01)
(52) U.S. Cl. ..................................................... 504/206
(58) Field of Classification Search ................ 504/206
See application file for complete search history.

(56) References Cited

U.S. PATENT DOCUMENTS

| | | | | |
|---|---|---|---|---|
| 4,159,901 A | * | 7/1979 | Beestman et al. .......... | 504/206 |
| 4,405,531 A | | 9/1983 | Franz ..................... | 260/501.12 |
| 6,030,923 A | * | 2/2000 | Okano et al. ............... | 504/362 |
| 6,277,788 B1 | | 8/2001 | Wright ....................... | 504/206 |
| 6,365,551 B1 | | 4/2002 | Wright et al. ............... | 504/206 |
| 2003/0087764 A1 | * | 5/2003 | Pallas et al. ................ | 504/365 |

FOREIGN PATENT DOCUMENTS

| WO | 97/16969 | 5/1997 |
|---|---|---|
| WO | 01/89302 | 11/2001 |
| WO | 02/21924 | 3/2002 |
| WO | 03/063589 | 8/2003 |

* cited by examiner

*Primary Examiner*—Sreeni Padmanabhan
*Assistant Examiner*—Renee Claytor
(74) *Attorney, Agent, or Firm*—Craig Mixan

(57) ABSTRACT

This invention relates to a high-strength herbicidal formulation containing high concentrations of glyphosate monomethylamine or dimethylamine salt and one or more surfactants selected to enhance the herbicidal activity of the glyphosate salts. The formulations exhibit significantly lower viscosity at high concentrations.

6 Claims, No Drawings

HIGH-STRENGTH, LOW VISCOSITY HERBICIDAL FORMULATIONS OF GLYPHOSATE

The present invention claims the benefit of U.S. Provisional Application Ser. No. 60/493,554 filed on Aug. 4, 2003.

BACKGROUND OF THE INVENTION

The present invention relates to high-strength, liquid formulations of N-phosphonomethyl glycine (glyphosate), more particularly, the monomethylamine (MMA) and the dimethylamine (DMA) salts of glyphosate.

Glyphosate is a known, effective herbicide. U.S. Pat. No. 4,405,531 discloses a long list of organic ammonium salts of glyphosate useful as herbicides, including the methylamine salt and dimethylamine salt, and, as an example, monoalkylammonium and dialkylammonium are listed as a particularly preferred salts. Various formulations are currently marketed, many of which are aqueous solutions that can be used as is or diluted prior to use. Typically the glyphosate is provided as a salt, which exhibits sufficiently high solubility in water to provide a high-strength herbicidal formulation. For example, U.S. Pat. No. 6,277,788 discloses both the isopropylamine salt (IPA) and the monoethanolamine (MEA) salt of glyphosate. Additionally, U.S. Pat. No. 6,365,551 and WO 01/89302 disclose various formulations that include the potassium (K) salt of glyphosate. A high-strength formulation is desirable for a variety of economic and environmental reasons. For example, it is desirable to provide a high-strength formulation to reduce shipping and handling costs and to reduce the amount of packaging material that must be disposed. The high-strength formulations should be stable and retain potency during storage and shipping. Furthermore, the high-strength formulation should be a clear, homogeneous liquid that is stable at temperatures at least as high as 50° C. and should not exhibit any precipitation at temperatures as low as 0° C.

The herbicidal formulations typically include an efficacy-enhancing surfactant. Inclusion of a surfactant is highly desirable because the resulting formulation exhibits a substantially increased herbicidal activity. WO 03/063589, for example, describes glyphosate formulations using alkylbetaine surfactants in combination with other surfactants. However, selected surfactants either can interact with the glyphosate salt, increasing the viscosity of the herbicidal formulation, or are generally incompatible with the glyphosate salt solution. Certain surfactants, for example, some of the surfactants in the oxyalkylene alkylamine class of compounds, when combined with the glyphosate salt, increase the viscosity of the formulation. If the viscosity is too high, handling of the concentrated herbicide can be difficult. Furthermore, highly viscous liquids are difficult to accurately measure, either for application to the plants or for dilution to a less concentrated spray solution. Depending upon the concentration and specific surfactant, the herbicidal formulation can form a gel, which makes most applications extremely difficult if not impossible to perform.

Formulations of the commonly used IPA salt of glyphosate become increasingly viscous at concentrations greater than 350 gram acid equivalent per liter (gae/l), particularly at concentrations greater than 440 gae/l. The high viscosity makes the formulation difficult to measure and pump, especially at the lower temperatures typically encountered at the beginning of the season.

A major limitation of the MEA and K salts of glyphosate is the incompatibility with a wide range of surfactants. In particular, U.S. Pat. No. 6,277,788 discloses that polyoxyethylene alkylamines are only compatible with the MEA salt of glyphosate when the sum of the total average number of carbon atoms plus the average number of oxyethylene groups is equal to or less than 25. Although the K salt of glyphosate offers the ability to form low viscosity, high strength glyphosate formulations, it has some significant limitations in that many surfactants commonly used to enhance the efficacy of glyphosate are not compatible with the glyphosate K salt solution. For example, commonly used alkylamine ethoxylate surfactants are only compatible (form a homogeneous mixture) when the degree of ethoxylation is no more than about 5. Alkylamine ethoxylate surfactants with low degree of ethoxylation have a higher potential to cause eye irritation, however, than alkylamine ethoxylate surfactants with a higher degree of ethoxylation, e.g. 15-20 mole ethylene oxide.

In light of the above described problems, there is a continuing need for additional improvements in the relevant fields including improved high-strength herbicidal formulations that exhibit low viscosity and which contain a suitably efficacious surfactant. The present invention addresses these needs and provides a wide variety of benefits and advantages.

SUMMARY OF THE INVENTION

It has now been found that the monomethylamine (MMA) and the dimethylamine (DMA) salts of glyphosate allow the preparation of high-strength liquid formulations at surprisingly low viscosity. Furthermore, sufficient amounts of one or more efficacy enhancing surfactants can be incorporated into the high-strength formulation while still maintaining a low viscosity profile. The present invention provides a high-strength herbicidal concentrate composition comprising: (a) water, (b) glyphosate, predominantly in the form of the MMA or the DMA salt, in solution in the water in an amount of greater than about 350 grams of acid equivalent per liter (gae/l) of the composition, and (c) at least one surfactant in a total amount of about 20 to about 200 grams per liter (g/l) of the composition.

The herbicidal formulation includes a herbicidally efficacious surfactant. This surfactant is selected to enhance the herbicidal activity of the formulation and to minimize the viscosity of the high-strength formulation. The MMA and DMA salts of glyphosate are compatible with a wide variety of surfactants. Preferred surfactants are selected from the following groups of surfactants:

(a) alkylamine and alkyletheramine surfactants having the chemical formula

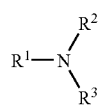

in which $R^1$ is a $C_8$-$C_{24}$, preferably a $C_{12}$-$C_{18}$, straight or branched chain, saturated or unsaturated hydrocarbyl group, optionally interrupted by one or more ether linkages, and $R^2$ and $R^3$ are independently $C_1$-$C_4$ alkyl, preferably methyl, groups or polyoxyalkylene chains having in total 2 to about 22 alkylene oxide units, preferably ethylene oxide units;

(b) quaternary ammonium surfactants having the chemical formula

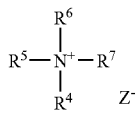

in which Z⁻ is an agriculturally acceptable anion such as chloride, bromide, iodide, sulfate or acetate and $R^4$, $R^5$, $R^6$ and $R^7$ include, without limitation, the following:
  (i) $R^4$ is a benzyl or a $C_8$-$C_{24}$, preferably a $C_{12}$-$C_{18}$, straight or branched chain, saturated or unsaturated hydrocarbyl group, optionally interrupted by one or more ether linkages, and $R^5$, $R^6$ and $R^7$ are independently $C_1$-$C_4$ alkyl, preferably methyl, groups;
  (ii) $R^4$ and $R^5$ are independently $C_8$-$C_{24}$, preferably $C_{12}$-$C_{18}$, straight or branched chain, saturated or unsaturated hydrocarbyl group, optionally interrupted by one or more ether linkages, and $R^6$ and $R^7$ are independently $C_1$-$C_4$ alkyl, preferably methyl, groups;
  (iii) $R^4$ is a $C_8$-$C_{24}$, preferably $C_{12}$-$C_{18}$, straight or branched chain, saturated or unsaturated hydrocarbyl group, optionally interrupted by one or more ether linkages, $R^5$ is a polyoxyalkylene chain having about 2 to about 22, preferably about 2 to about 15, $C_2$-$C_4$ alkylene oxide units, preferably ethylene oxide units, and $R^6$ and $R^7$ are independently $C_1$-$C_4$ alkyl, preferably methyl, groups; or
  (iv) $R^4$ is a $C_8$-$C_{24}$, preferably $C_{12}$-$C_{18}$, straight or branched chain, saturated or unsaturated hydrocarbyl group, optionally interrupted by one or more ether linkages, $R^5$ and $R^6$ are polyoxyalkylene chains having about 2 to about 22, preferably about 2 to about 15, $C_2$-$C_4$ alkylene oxide units, preferably ethylene oxide units, and $R^7$ is a $C_1$-$C_4$ alkyl, preferably methyl, group;
(c) amphoteric surfactants having the chemical formula

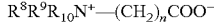

in which $R^8$, $R^9$, $R_{10}$ and n include, without limitation, the following:
  (v) $R^8$ is a $C_8$-$C_{24}$, preferably a $C_{12}$-$C_{18}$, straight or branched chain, saturated or unsaturated hydrocarbyl group, and $R^9$ and $R_{10}$ are independently $C_1$-$C_4$ alkyl, preferably methyl, groups or a hydrogen atom; and n is an integer between 1 to 5; or
  (vi) $R^8$ is a [$R^{11}$—CONH—$(CH_2)_x$—] radical where $R^{11}$ is a $C_8$-$C_{24}$, preferably a $C_{12}$-$C_{18}$, straight or branched chain, saturated or unsaturated hydrocarbyl group, x is an integer between 1 to 5, and $R^9$ and $R^{10}$ are independently $C_1$-$C_4$ alkyl, preferably methyl, groups or a hydrogen atom; and n is an integer between 1 to 5;
(d) alcohol ethoxylates having the chemical formula

in which formula $R^{12}$ is a $C_8$-$C_{24}$, preferably a $C_{12}$-$C_{18}$, straight or branched chain, saturated or unsaturated hydrocarbyl group, $R^{13}$ represents independently a hydrogen atom or a methyl or ethyl radical, preferably a hydrogen atom, n is an integer between 2 and 50, preferably between 10 and 30, and $R^{14}$ is a $C_1$-$C_4$ alkyl, preferably methyl, group or a hydrogen atom;
(e) alcohol ethoxylate phosphate esters having the chemical formula

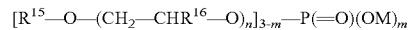

in which formula $R^{15}$ is a $C_6$-$C_{20}$, preferably a $C_8$-$C_{18}$, straight or branched chain, saturated or unsaturated hydrocarbyl group, $R^{16}$ represents independently a hydrogen atom or a methyl or ethyl radical, preferably a hydrogen atom, n is an integer between 0 and 10, preferably in the range 2 to 10, M represents independently a hydrogen atom, an alkali or alkaline-earth metal, an ammonium or an alkylammonium ion, and m is a whole number in the range 1 to 2;
(f) alkylpolyglycosides having the general chemical formula

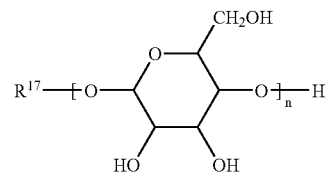

in which the polyglycoside is derived from glucose or other mono-, di- or polysaccharides, n is the degree of polymerisation and is typically within the range from 1 to 3, and $R^{17}$ is a $C_6$-$C_{18}$, preferably a $C_8$-$C_{10}$, straight or branched chain, saturated or unsaturated hydrocarbyl group;
(g) anionic ester derivatives of alkylpolyglycosides having the chemical formula

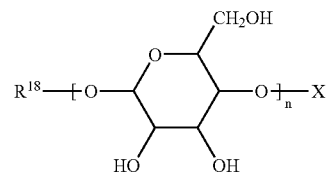

in which the polyglycoside is derived from glucose or other mono-, di- or polysaccharides, n is the degree of polymerisation and is typically within the range from 1 to 3, $R^{18}$ is a $C_6$-$C_{18}$, preferably a $C_8$-$C_{10}$, straight or branched chain, saturated or unsaturated hydrocarbyl group, and X represents a carboxylate moiety derived from a bi- or tri-carboxylic acid, preferably citric, tartaric or sulfosuccinic acid (see European patent EP 0 258 814 B1); or
(h) mixtures thereof.

The MMA and DMA salts of glyphosate provide certain advantages over other salts that have been commercialized. They are compatible with alkylamine ethoxylates with high degrees of ethoxylation which are less prone to exhibit eye irritation. In addition, tank mixtures of glyphosate K salt with other herbicide acid salts (e.g. triclopyr, 2,4-D) can form poorly soluble potassium salts of the second herbicide acid, thus reducing the biological effectiveness of the second herbicide. The MMA and DMA salts overcome this incompatibility issue. Furthermore, the MMA and DMA salts have a lower molecular weight than the IPA or MEA salts. Thus, at a given salt concentration, the MMA or the DMA salt of glyphosate has a higher glyphosate acid equivalent content than the IPA salt or the recently described MEA salt.

In still yet another form, the present invention provides a method of treating plants with a herbicidal formulation. The formulation can be provided as described above. The formulation is typically applied as a post-emergent herbicide. The formulation can be applied as a highly concentrated solution or preferably is diluted with water prior to application to the plants. In addition, the MMA salt of glyphosate is particularly more effective than other salts in controlling lambsquarters.

DETAILED DESCRIPTION OF THE INVENTION

In general the present invention is directed to a high-strength herbicidal concentrate composition containing the MMA or the DMA salt of glyphosate and an efficacious surfactant. More specifically, the present invention provides a high-strength herbicidal concentrate composition comprising: (a) water, (b) glyphosate, predominantly in the form of the MMA or the DMA salt, in solution in the water in an amount of greater than about 350 (gae/l) of the composition, and (c) at least one surfactant in a total amount of about 20 to about 200 (g/l) of the composition.

The herbicidal formulation includes the glyphosate salt in an amount sufficient to provide the high-strength formulation. In preferred embodiments, the high-strength herbicidal formulation includes greater than about 350 gae/l based upon the glyphosate acid equivalent of the glyphosate salt; more preferably, the high-strength herbicidal formulation includes greater than about 440 gae/l based upon the glyphosate acid equivalent of the glyphosate salt; most preferably, the high-strength herbicidal formulation includes greater than about 480 gae/l based upon the glyphosate acid equivalent of the glyphosate salt.

In preferred embodiments, the present invention includes a high-strength herbicidal formulation that is storage stable at high temperatures. That is, the formulation forms a clear, homogeneous, stable solution that does not exhibit cloudiness under the storage conditions. More preferably, the formulations of the present invention are stable at temperatures greater than or equal to about 50° C., more preferably, at temperature equal to or greater than about 60° C.

Furthermore, the herbicidal formulation also does not exhibit separation or precipitation (or crystallization) of any of the components at low temperatures. For example, the high-strength formulation remains a clear solution at temperatures below about 10° C., more preferably at temperatures below about 0° C.

The term "predominantly" in the above context means that at least 50 percent, preferably at least 75 percent and more preferably at least 90 percent by weight of the glyphosate, expressed as acid equivalents, is present as the MMA or DMA salt. The balance can be made up of other salts, such as the IPA salt, provided that the formulation remains a clear, homogeneous liquid that is stable at temperatures at least as high as 50° C. and does not exhibit any precipitation at temperatures as low as 10° C.

The high-strength herbicidal formulation also includes an efficacy-enhancing amount of a surfactant. In preferred embodiments, the surfactant is selected to be compatible in solution with the high concentration of the glyphosate in the herbicidal formulation. By use of the term "compatible" in the present application, it will be understood by those skilled in the art to include within its meaning that the resulting solution does not exhibit a phase separation or precipitation in the formulation that can be initially observed as a cloudiness and which is typically determined at a specified temperature.

The surfactant for use in the present invention is preferably selected to include one or more of the following types of compounds: alkoxylated alkylamine surfactants having 8 to 22 carbon atoms and a total of 1-20 alkylene oxide groups, available for example from Akzo Nobel as Ethomeen™ C/15, Ethomeen T/15, and Ethomeen T/20 respectively; etheramine surfactants, such as Tomah E-14-2, Tomah E-14-5 and Tomah E-17-5 respectively; quaternary ammonium surfactants, such as Ethoquad™ C/12, Ethoquad 18/12 or Tomah Q-14-2; amphoteric surfactants, such as Geronol™ CF/AS 30 from Rhodia or Tego™ Betaine F 50 from Goldschmidt; alcohol ethoxylates, such as Tergitol™ 15S20; alcohol ethoxylate phosphate esters such as Geranol CF/AR from Rhodia; alkylpolyglycosides such as Akzo Nobel AG 6202 or AG 6210; or anionic ester derivatives of alkylpolyglycosides such as the Eucarol™ AGE surfactants.

The surfactant can be included in the herbicidal formulation in a desired concentration. Preferably the desired concentration is sufficient to enhance the herbicidal activity of the resulting formulation over that observed with a comparable herbicidal formulation without the surfactant. More preferably, the herbicidal formulation includes the surfactant in amounts between about 20 g/l and about 200 g/l, more preferably in amount between about 100 g/l and about 150 g/l.

It has unexpectedly been determined that, with a judicious selection of a specific surfactant in combination with the MMA or the DMA salt of glyphosate, the viscosity of the resulting herbicidal formulation is greatly improved. Most preferred are mixtures of surfactants. For example, a blend of tallowamine ethoxylate with an amphoteric surfactant like Geronol CF/AS 30 shows a synergistic effect on viscosity, i.e., the viscosity of the formulation containing the blend of surfactants is significantly lower than that of formulations containing individual surfactants at the same concentration. In preferred embodiments, the herbicidal formulation is provided to exhibit a viscosity of less than about 140 centipoise (140 milliPascal·s; mPa·s), more preferably less than about 100 centipoise (100 mPa·s).

Furthermore, selected combinations of surfactant and MMA or DMA salt of glyphosate remain compatible in the formulation at high concentration. The resulting aqueous composition can be provided as a high strength herbicidal formulation.

The formulations described herein can be applied to plants in an amount sufficient to induce a herbicidal effect. For example, a formulation prepared according the present invention can be applied as an aqueous solution to plants including the plants' leaves, stems, branches, flowers and/or fruit. The herbicidal formulation can be applied in a herbicidally effective amount sufficient to inhibit plant growth or kill individual plants.

The agricultural compositions prepared according to the present invention are highly effective as a herbicide composition against a variety of weeds. The formulations of the present invention can be used as is or combined with other components including other agriculturally acceptable adjuvants commonly used in formulated agricultural products, such as antifoam agents, compatibilizing agents, sequestering agents, neutralizing agents and buffers, corrosion inhibitors, dyes, odorants, penetration aids, wetting agents, spreading agents, dispersing agents, thickening agents, freeze point depressants, antimicrobial agents, crop oil, other biologically and/or agriculturally active components and the like. The concentrated agricultural formulations are typically diluted in water and then applied by conventional means well known to those in the art.

EXAMPLE 1

Preparation of High-Strength Glyphosate DMA Salt Formulation

A glyphosate DMA salt concentrate was prepared by reacting 408 g glyphosate technical wetcake with 283 g of a 40% aqueous dimethylamine solution in 61 g water. The concentrate contained 62% glyphosate DMA salt. The solution has a density of 1.259 g/ml.

Formulations were prepared by blending the concentrate with the appropriate amount of surfactant and water. The examples given in Table 1 demonstrate the invention.

TABLE 1

Formulation Examples

| Formulation Reference | g/l glyphosate acid equivalent as the DMA salt | Surfactant |
|---|---|---|
| 1 | 360 | Ethomeen C/15, 100 g/l |
| 2 | 360 | Ethoquad C/12, 100 g/l |
| 3 | 360 | Tomah Q-14-2, 100 g/l |
| 4 | 360 | PEG-20 Tallowamine, 100 g/l |
| 5 | 540 | PEG-10 Tallowamine, 100 g/l |
| 6 | 480 | PEG-5 Tallowamine, 110 g/l |
| 7 | 480 | PEG-10 Tallowamine, 150 g/l |
| 8 | 480 | Geronol CF/AS 30, 150 g/l |
| 9 | 480 | Geronol CF/AS 30, 120 g/l + PEG-10 Tallowamine, 30 g/l |
| 10 | 480 | Akzo Nobel AG 6202, 130 g/l |
| 11 | 480 | Geronol CF/AR, 120 g/l |
| 12 | 480 | Eucarol AGE/ET, 100 g/l |
| 13 | 480 | Tego Betaine F50, 80 g/l + PEG-10 Tallowamine, 60 g/l |

Ethomeen C/15 is a PEG-5 cocoalkylamine
Ethoquad C/12 is a Cocoalkylmethylbis(2-hydroxyethyl) ammonium chloride
Tomah Q-14-2 is a Isodecyloxypropyl methyl bis(2-hydroxyethyl) ammonium chloride
Geronol CF/AS 30 is an $C_{12}$-$C_{14}$ alkyldimethyl betaine
Akzo Nobel AG 6202 is an alkylpolyglucoside
Geronol CF/AR is an alcohol ethoxylate phosphate ester
Eucarol AGE/ET is an alkylpolyglucoside tartaric acid ester
Tego Betaine F50 is a cocamidopropyl betaine All formulations form clear, homogeneous liquids. The formulations were storage stable for 2 weeks at 54° C. with no phase separation and 2 weeks at −10° C. without crystallization. The cloud point of the above formulations was greater than 60° C.

The viscosity of the sample formulations was measured with a Brookfield LVT viscometer or a Bohlin CS-50 Rheometer and compared against commercially available high-strength formulations. Surprisingly, the viscosity of the high-strength glyphosate DMA salt formulations was significantly lower than those of the commercial standards (see Table 2).

Unexpectedly, formulation 9, which was prepared by blending 4 parts of formulation 8 with 1 part of formulation 7, has a lower viscosity than either one of the two formulations alone. Following a simple mixing rule the expected viscosity would be 249 mPa·s, whereas the actual viscosity was only 59 mPa·s at the same total surfactant concentration. This demonstrates the synergistic viscosity effect of blending the two surfactants.

TABLE 2

Formulation Viscosities

| Sample | Viscosity |
|---|---|
| Roundup UltraMAX (USA) (445 gae/l glyphosate IPA) | 185 mPa · s |
| Roundup MAX (Australia) (510 gae/l glyphosate MEA) | 176 mPa · s |
| Glyphomax Plus (USA) (356 gae/l glyphosate IPA) | 56 mPa · s |
| 5 (540 gae/l glyphosate DMA-Salt) | 100 mPa · s |
| 6 (480 gae/l glyphosate DMA-Salt) | 96 mPa · s |
| 7 (480 gae/l glyphosate DMA-Salt) | 82 mPa · s |
| 8 (480 gae/l glyphosate DMA-Salt) | 291 mPa · s |
| 9 (480 gae/l glyphosate DMA-Salt) | 59 mPa · s |
| 10 (480 gae/l glyphosate DMA-Salt) | 72 mPa · s |
| 11 (480 gae/l glyphosate DMA-Salt) | 42 mPa · s |
| 12 (480 gae/l glyphosate DMA-Salt) | 32 mPa · s |
| 13 (480 gae/l glyphosate DMA-Salt) | 68 mPa · s |

EXAMPLE 2

Efficacy of High-Strength Glyphosate DMA Salt Formulation

The glyphosate DMA salt formulations were evaluated for efficacy against a range of 5 dicot and 3 monocot weeds in a greenhouse trial. The formulations were applied at 100, 200, 400, 600 and 800 gae/ha with Roundup Ultra™ Herbicide, Roundup UltraMAX™ and Roundup WeatherMAX™ Herbicide (all Monsanto) as the standard treatments. Spray volume was 187 liters per hectare (l/ha); weeds were at the 3 leaf stage at the time of application. Each treatment was replicated three times; evaluation was done at 14 days after application by visual assessment of % control.

Table 3 shows the percent control for individual weed species at the application rate of 600 gae/ha.

TABLE 3

Biological Efficacy of Example Formulations (360 gae/l glyphosate DMA salt) compared with Roundup Ultra (356 gae/l glyphosate IPA salt) at an application rate of 600 gae/ha. Percent Control measured 14 days after application

| Formulation | IPOHE | CHEAL | EPHHL | ABUTH | CASOB | ECHCG | AVEFA | AGGRE | Ave. |
|---|---|---|---|---|---|---|---|---|---|
| Roundup Ultra | 41.7% | 80.9% | 84.2% | 80.0% | 70.0% | 85.9% | 53.3% | 51.7% | 68.4% |
| 1 | 43.3% | 89.2% | 90.0% | 76.7% | 80.8% | 93.3% | 74.2% | 78.4% | 78.2% |

TABLE 3-continued

Biological Efficacy of Example Formulations (360 gae/l glyphosate DMA salt)
compared with Roundup Ultra (356 gae/l glyphosate IPA salt) at an application rate
of 600 gae/ha. Percent Control measured 14 days after application

| Formulation | IPOHE | CHEAL | EPHHL | ABUTH | CASOB | ECHCG | AVEFA | AGGRE | Ave. |
|---|---|---|---|---|---|---|---|---|---|
| 2 | 50.0% | 85.9% | 89.0% | 79.2% | 78.4% | 90.7% | 68.3% | 69.2% | 76.3% |
| 3 | 43.3% | 84.2% | 92.5% | 80.0% | 78.4% | 88.2% | 68.4% | 65.9% | 75.1% |

| | | |
|---|---|---|
| IPOHE | Ipomoea hederacea | morningglory |
| CHEAL | Chenopodium album | lambsquarter |
| EPHHL | Euphorbia heterophylla | wild pointsettia |
| ABUTH | Abutilon theophrasti | velvet leaf |
| CASOB | Cassia obtusifolia | sicklepod |
| ECHCG | Echinochloa crus-galli | barnyardgrass |
| AVEFA | Avena fatua | wild oat |
| AGGRE | Agropyron repens | quackgrass |

On average, the efficacy of the DMA salt formulations (including only 100 g/l surfactant) was superior to the efficacy of the commercial IPA salt formulation (including 180 g/l surfactant) across the 8 species tested.

Table 4 shows the biological efficacy of the 480 gae/l glyphosate DMA salt formulation 6 compared with the commercial high-strength formulation Roundup UltraMAX. Across all species the DMA salt formulation performs better than the commercial IPA salt formulation.

On average, the efficacy of the DMA salt formulations was superior to the efficacy of the commercial IPA salt formulation across the 8 species tested.

In a further greenhouse study, the efficacy of a glyphosate DMA salt solution in mixture with DMA 4 (456 g/l 2,4-D acid equivalent in the form of the DMA salt) and Garlon 3A (360 g/l triclopyr acid equivalent in the form of the triethylamine [TEA] salt) respectively was compared with the efficacy of a glyphosate K salt solution in the same mixtures.

TABLE 4

Biological Efficacy of Example Formulation 6 (480 gae/l glyphosate DMA Salt)
compared with the commercial standard Roundup UltraMAX (445 gae/l glyphosate
IPA salt) at an application rates of 600 gae/ha. Percent Control
measured 14 days after application

| Formulation | IPOHE | CHEAL | EPHHL | ABUTH | CASOB | ECHCG | AVEFA | AGGRE | Ave. |
|---|---|---|---|---|---|---|---|---|---|
| Roundup UltraMAX | 61.7% | 83.3% | 94.7% | 85.0% | 66.7% | 99.0% | 66.7% | 53.3% | 76.3% |
| 6 | 78.3% | 85.0% | 99.0% | 86.7% | 68.3% | 91.0% | 81.7% | 78.3% | 83.5% |

On average, the efficacy of the DMA salt formulations was superior to the efficacy of the commercial IPA salt formulation across the 8 species tested.

Table 5 compares the biological efficacy of the 480 gae/l glyphosate DMA salt formulation 7 and 540 gae/l glyphosate DMA salt formulation 5 compared with the commercial high-strength formulation Roundup WeatherMAX (540 gae/l glyphosate K salt). Across all species the DMA salt formulations perform better than the commercial K salt formulation.

The glyphosate salt solutions were prepared by diluting the glyphosate DMA salt concentrate and glyphosate K salt concentrate with the required amount of water to prepare solutions containing 480 g/l glyphosate acid equivalent each. Five broadleaf species (IPOHE, CHEAL, EPHHL, ABUTH and CASOB) were sprayed with the individual formulations as well as the mixtures listed in Table 6. The herbicide interactions were analyzed using Colby's equation. This equation for the expected mixture response is:

$$Y_{1+2} = Y_1 + Y_2 - (Y_1 Y_2)100$$

TABLE 5

Biological Efficacy of Example Formulations 5 (540 gae/l glyphosate DMA Salt) and
7 (480 gae/l glyphosate DMA Salt) compared with the commercial standard Roundup
WeatherMAX (540 gae/l glyphosate K salt) at an application rates of 600 gae/ha.
Percent Control measured 14 days after application

| Formulation | IPOHE | CHEAL | EPHHL | ABUTH | CASOB | ECHCG | AVEFA | AGGRE | Ave. |
|---|---|---|---|---|---|---|---|---|---|
| Roundup WeatherMAX | 43.3% | 81.7% | 91.7% | 75.0% | 86.7% | 75.0% | 88.3% | 97.0% | 79.8% |
| 5 | 61.7% | 83.3% | 98.3% | 91.7% | 83.3% | 86.7% | 92.0% | 90.0% | 85.9% |
| 7 | 55.0% | 76.7% | 97.0% | 97.3% | 83.3% | 95.0% | 90.0% | 99.3% | 86.7% | where $Y_{1+2}$ is the expected mixture response and $y_1$ and $y_2$ are the percent control values of the individual herbicides.

TABLE 6

Biological Efficacy of glyphosate DMA salt (480 gae/l glyphosate DMA Salt) and glyphosate K salt (480 gae/l glyphosate K Salt) in mixture with a second herbicide at an application rate of 420 gae/ha glyphosate and 140 gae/ha of the second herbicide. Percent Control measured 3 days after application and averaged over the 5 species

|  | % Actual Control | % Expected Control | Actual − Expected Control |
|---|---|---|---|
| 420 gae/ha glyphosate K salt | 35.7 |  |  |
| 420 gae/ha glyphosate DMA salt | 35.7 |  |  |
| 140 gae/ha 2,4-D DMA salt | 47.0 |  |  |
| 140 gae/ha triclopyr TEA salt | 55.0 |  |  |
| 420 gae/ha glyphosate K salt + 140 gae/ha 2,4-D DMA salt | 50.7 | 65.9 | −15.2 |
| 420 gae/ha glyphosate DMA salt + 140 gae/ha 2,4-D DMA salt | 67.0 | 65.9 | 1.1 |
| 420 gae/ha glyphosate K salt + 140 gae/ha triclopyr TEA salt | 57.7 | 71.1 | −13.4 |
| 420 gae/ha glyphosate DMA salt + 140 gae/ha triclopyr TEA salt | 72.0 | 71.1 | 0.9 |

The results show that the glyphosate K salt is antagonistic to both 2,4-D DMA and triclopyr TEA as seen in the reduced actual control compared with the expected control using Colby's equation. In contrast, the glyphosate DMA salt shows no antagonism with the actual control being equivalent to the expected control, thus providing a significant improvement over the glyphosate K salt.

EXAMPLE 3

Preparation of High-Strength Glyphosate MMA Salt Formulation

A glyphosate MMA salt concentrate was prepared by reacting 505 g glyphosate technical wetcake with 238 g of a 41% aqueous methylamine solution in 121 g water. The concentrate contained 62% glyphosate MMA salt. The solution has a density of 1.302 g/ml.

Formulations were prepared by blending the concentrate with the appropriate amount of surfactant and water. The examples given in Table 7 demonstrate the invention.

TABLE 7

Formulation Examples

| Formulation Reference | g/l glyphosate acid equivalent as the MMA salt | Surfactant |
|---|---|---|
| 14 | 480 | PEG-5 Tallowamine, 150 g/l |
| 15 | 480 | PEG-10 Tallowamine, 150 g/l |
| 16 | 480 | Geronol CF/AS 30, 150 g/l |
| 17 | 480 | Akzo Nobel AG 6210, 130 g/l |
| 18 | 480 | Geronol CF/AR, 120 g/l |
| 19 | 480 | Eucarol AGE/EC, 100 g/l |
| 20 | 480 | PEG-10 Tallowamine, 50 g/l Geronol CF/AS 30, 100 g/l |
| 21 | 480 | PEG-10 Tallowamine, 50 g/l PEG-5 Tallowamine, 20 g/l Geronol CF/AS 30, 100 g/l |
| 22 | 540 | PEG-10 Tallowamine, 33 g/l PEG-5 Tallowamine, 17 g/l Geronol CF/AS 30, 100 g/l |

Geronol CF/AS 30 is an $C_{12}$-$C_{14}$ alkyldimethyl betaine
Akzo Nobel AG 6210 is an alkylpolyglucoside
Geronol CF/AR is an alcohol ethoxylate phosphate ester
Eucarol AGE/EC is an alkylpolyglucoside citric acid ester All formulations form clear, homogeneous liquids. The formulations were storage stable for 2 weeks at 54° C. with no phase separation and 2 weeks at −10° C. without crystallization. The cloud point of the above formulations was greater than 60° C.

The viscosity of the sample formulations was measured with a Brookfield LVT viscometer or a Bohlin CS-50 Rheometer and compared against some commercially available high-strength formulations. Surprisingly, the viscosity of the high-strength glyphosate MMA salt formulations was significantly lower than those of the commercial standards (see Table 8).

TABLE 8

Formulation Viscosities
Viscosity Measurement, Brookfield LVT, Spindle #2 at 20° C.

| Sample | Viscosity (mPa · s) |
|---|---|
| Roundup UltraMAX (USA) (445 gae/l glyphosate IPA) | 161 |
| Roundup MAX (Australia) (510 gae/l glyphosate MEA) | 153 |
| Roundup WeatherMAX (USA) (540 gae/l glyphosate potassium) | 52 |
| 15 (480 gae/l glyphosate MMA-Salt) | 56 |
| 16 (480 gae/l glyphosate MMA-Salt) | 163 |
| 17 (480 gae/l glyphosate MMA-Salt) | 41 |
| 18 (480 gae/l glyphosate MMA-Salt) | 25 |
| 19 (480 gae/l glyphosate MMA-Salt) | 28 |
| 20 (480 gae/l glyphosate MMA-Salt) | 28 |
| 21 (480 gae/l glyphosate MMA-Salt) | 45 |
| 22 (540 gae/l glyphosate MMA-Salt) | 90 |

Surprisingly, sample 20, which was prepared by blending 1 part of formulation 15 with 2 parts of formulation 16, has a lower viscosity than either one of the two formulations alone. If the viscosity were following a simple mixing rule the expected viscosity would be about 130 mPa·s. The measured viscosity of only 28 mPa·s demonstrates the synergistic effect of blending the two surfactants.

EXAMPLE 4

Efficacy of High-Strength Glyphosate MMA Salt Formulation

The glyphosate MMA salt formulations were evaluated for efficacy against a range of 5 dicot and 3 monocot weeds in a greenhouse trial. The formulations were applied at 100, 200, 400, 600 and 800 gae/ha with Roundup WeatherMAX Herbicide (Monsanto) as the standard treatment. Spray volume was 140 liters per hectare (l/ha); weeds were at the 3 leaf stage at the time of application. Each treatment was replicated three times; evaluation was done at 14 days after application by visual assessment of % control.

Table 9 shows the percent control for individual weed species at the application rate of 400 gae/ha.

TABLE 9

Biological Efficacy of Example Formulations (480/540 gae/l glyphosate MMA salt) compared with Roundup WeatherMAX (540 gae/l glyphosate K salt) at an application rate of 400 gae/ha. Percent Control measured 14 days after application

| Formulation | IPOHE | CHEAL | EPHHL | ABUTH | CASOB | ECHCG | AVEFA | AGGRE | Ave. |
|---|---|---|---|---|---|---|---|---|---|
| Roundup WeatherMAX | 73.3 | 70.0 | 70.0 | 70.0 | 70.0 | 76.0 | 56.7 | 63.3 | 68.7 |
| 20 | 66.7 | 98.3 | 90.0 | 60.0 | 75.0 | 84.7 | 75.0 | 71.7 | 77.7 |
| 21 | 63.3 | 99.0 | 89.7 | 68.3 | 75.0 | 90.0 | 63.3 | 75.0 | 78.0 |
| 22 | 68.3 | 98.3 | 92.3 | 75.0 | 60.0 | 97.0 | 76.7 | 73.3 | 80.1 |

20: 480 gae/l glyphosate MMA salt
21: 480 gae/l glyphosate MMA salt
22: 540 gae/l glyphosate MMA salt

| IPOHE | *Ipomoea hederacea* | morningglory |
| CHEAL | *Chenopodium album* | lambsquarter |
| EPHHL | *Euphorbia heterophylla* | wild pointsettia |
| ABUTH | *Abutilon theophrasti* | velvet leaf |
| CASOB | *Cassia obtusifolia* | sicklepod |
| ECHCG | *Echinochloa crus-galli* | barnyardgrass |
| AVEFA | *Avena fatua* | wild oat |
| AGGRE | *Agropyron repens* | quackgrass |

On average, the efficacy of the MMA salt formulations was superior to the efficacy of the commercial glyphosate K salt formulation across the 8 species tested.

Table 10 shows a comparison of the $GR_{90}$ values at 9 days after application of the glyphosate MMA salt formulations 20, 21 and 22 compared with the commercial high-strength formulation Roundup WeatherMAX on lambsquarter, a particularly troublesome weed in the Midwest USA region.

TABLE 10

$GR_{90}$ values on lambsquarter of Example Formulations (480/540 gae/l glyphosate MMA salt) compared with Roundup WeatherMAX (540 gae/l glyphosate K salt)

|  | High | Low | $GR_{90}$ |
|---|---|---|---|
| Roundup WeatherMAX | 724 gae/ha | 476 gae/ha | 587 gae/ha |
| MMA 480 gae/l (20) | 513 gae/ha | 351 gae/ha | 425 gae/ha |
| MMA 480 gae/l (21) | 391 gae/ha | 222 gae/ha | 295 gae/ha |
| MMA 540 gae/l (22) | 472 gae/ha | 303 gae/ha | 378 gae/ha |

The $GR_{90}$ values, the amount in gae/ha required to provide 90% control of lambsquarter, are significantly lower for the glyphosate MMA formulation compared with the commercial Roundup WeatherMAX formulation (The high and low values in Table 10 reflect the 95% confidence interval). In particular, the glyphosate MMA salt formulation 20 requires only half the amount of glyphosate acid equivalent per hectare compared with the commercial standard Roundup WeatherMAX to achieve the same level of lambsquarter control.

What is claimed is:

1. A clear, homogenous, stable high-strength herbicidal concentrate composition, having a viscosity of less than 140 centipoise, consisting essentially of: (a) water, (b) glyphosate, predominantly in the form of the monomethylamine or the dimethylamine salt, in solution in the water in an amount of greater than about 350 grams of acid equivalent per liter of the composition, and (c) at least one surfactant in a total amount of about 20 to about 200 grams per liter of the composition in which the surfactant is a) an alkyletheramine surfactant having the chemical formula

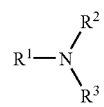

in which $R^1$ is a $C_8$-$C_{24}$ straight or branched chain, saturated or unsaturated hydrocarbyl group, optionally interrupted by one or more ether linkages, and $R^2$ and are independently polyoxyalkylene chains having in total 2 to about 22 alkylene oxide units;

b) a quaternary ammonium surfactant having the chemical formula

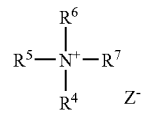

in which Z is an agriculturally acceptable anion and $R^4$, $R^5$, $R^6$ and $R^7$ include, without limitation, the following:

(i) $R^4$ is a benzyl or a $C_8$-$C_{24}$ straight or branched chain, saturated or unsaturated hydrocarbyl group, optionally interrupted by one or more ether linkages, and $R^5$, $R^6$ and $R^7$ are independently $C_1$-$C_4$ alkyl groups;

(ii) $R^4$ and $R^5$ are independently a $C_8$-$C_{24}$ straight or branched chain, saturated or unsaturated hydrocarbyl group, optionally interrupted by one or more ether linkages, and $R^6$ and $R^7$ are independently $C_1$-$C_4$ alkyl groups;

(iii) $R^4$ is a $C_8$-$C_{24}$ straight or branched chain, saturated or unsaturated hydrocarbyl group, optionally interrupted by one or more ether linkages, $R^5$ is a polyoxyalkylene chain having about 2 to about 22 $C_2$-$C_4$ alkylene oxide units, and $R^6$ and $R^7$ are independently $C_1$-$C_4$ alkyl groups; or (iv) $R^4$ is a $C_8$-$C_{24}$ straight or branched chain, saturated or unsaturated hydrocarbyl group, optionally interrupted by one or more ether linkages, $R^5$ and $R^6$ are polyoxyalkylene chains having about 2 to about 22 $C_2$-$C_4$ alkylene oxide units, and $R^7$ is a $C_1$-$C_4$ alkyl group;

c) an amphoteric surfactant having the chemical formula

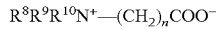

in which $R^8$, $R^9$, $R^{10}$ and n include, without limitation, the following:
(v) $R^8$ is a $C_8$-$C_{24}$ straight or branched chain, saturated or unsaturated hydrocarbyl group, and $R^9$ and $R^{10}$ are independently $C_1$-$C_4$ alkyl groups or a hydrogen atom; and n is an integer between 1 to 5; or
(vi) $R^8$ is a [$R^{11}$—CONH—$(CH_2)_x$—] radical where $R^{11}$ is a $C_8$-$C_{24}$ straight or branched chain, saturated or unsaturated hydrocarbyl group, x is an integer between 1 to 5, and $R^9$ and $R^{10}$ are independently $C_1$-$C_4$ alkyl groups or a hydrogen atom; and n is an integer between 1 to 5;

d) an alcohol ethoxylate having the chemical formula

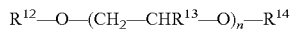

in which formula $R^{12}$ is a $C_8$-$C_{24}$ straight or branched chain, saturated or unsaturated hydrocarbyl group, $R^{13}$ represents independently a hydrogen atom or a methyl or ethyl radical, n is an integer between 2 and 50 and $R^{14}$ is a $C_1$-$C_4$ alkyl group or a hydrogen atom;

e) an alcohol ethoxylate phosphate ester having the chemical formula

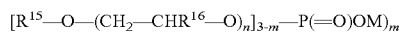

in which formula $R^{15}$ is a $C_6$-$C_{20}$ straight or branched chain, saturated or unsaturated hydrocarbyl group, $R^{16}$ represents independently a hydrogen atom or a methyl or ethyl radical, n is an integer between 0 and 10, M represents independently a hydrogen atom, an alkali or alkaline-earth metal, an ammonium or an alkylammonium ion, and m is a whole number in the range 1 to 2;

f) an alkylpolyglycoside having the general chemical formula

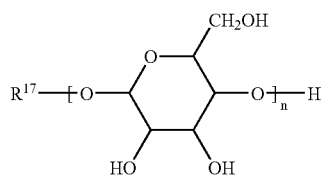

in which the polyglycoside is derived from glucose or other mono-, di- or polysaccharides, n is the degree of polymerisation and is typically within the range from 1 to 3, and $R^{17}$ is a $C_6$-$C_{18}$ straight or branched chain, saturated or unsaturated hydrocarbyl group;

g) an anionic ester derivative of alkylpolyglycosides having the chemical formula

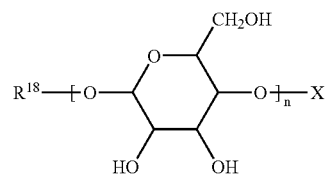

in which the polyglycoside is derived from glucose or other mono-, di- or polysaccharides, n is the degree of polymerisation and is typically within the range from 1 to 3, $R^{18}$ is a $C_6$-$C_{18}$ straight or branched chain, saturated or unsaturated hydrocarbyl group, and X represents a carboxylate moiety derived from a bi- or tri-carboxylic acid; or h) mixtures thereof.

2. A composition of claim 1 which contains greater than about 440 grams of acid equivalent of glyphosate per liter of the composition.

3. A composition of claim 1 having a viscosity of less than 100 centipoise.

4. A composition of claim 1 in which the surfactant is a mixture of a blend of tallowamine ethoxylates and a blend of amphoteric surfactants having the formula

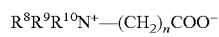

in which $R^8$ is a $C_{12}$-$C_{14}$ hydrocarbyl group, $R^9$ and $R^{10}$ are both $CH_3$ and n is 1.

5. A composition of claim 4 in which the viscosity is less than 100 centipoise and which contains greater than about 480 grams of acid equivalent of glyphosate per liter of composition.

6. A method of controlling undesirable vegetation which comprises applying to the vegetation a water-diluted composition of claim 1.

* * * * *